United States Patent [19]

Kane et al.

[11] 4,289,917

[45] Sep. 15, 1981

[54] ALKOXIDES OF 2-PINANOL

[75] Inventors: Bernard J. Kane, Atlantic Beach; Sean G. Traynor, Jacksonville, both of Fla.

[73] Assignee: SCM Corporation, New York, N.Y.

[21] Appl. No.: 67,522

[22] Filed: Aug. 17, 1979

Related U.S. Application Data

[63] Continuation-in-part of Ser. No. 25,734, Mar. 30, 1979, abandoned.

[51] Int. Cl.³ .............................................. C07C 1/253
[52] U.S. Cl. .................................... 585/359; 560/174; 585/363; 585/375; 585/378; 585/379
[58] Field of Search ....................... 585/363, 665, 359

[56] References Cited

U.S. PATENT DOCUMENTS

| | | | |
|---|---|---|---|
| 3,213,155 | 10/1965 | Schriesheim et al. | 585/665 |
| 3,270,084 | 8/1966 | Schriesheim et al. | 585/665 |
| 3,278,623 | 10/1966 | Derfer | 585/363 |
| 3,399,244 | 8/1968 | Qut et al. | 585/363 |
| 4,136,126 | 1/1979 | Hirschy et al. | 252/522 R |

OTHER PUBLICATIONS

J. R. Salmon et al., J. Chem. Soc. (B), p. 1249, 1971.
W. D. Burrows et al., J. Amer. Chem. Soc. 81, p. 245, 1958.

*Primary Examiner*—Curtis R. Davis
*Attorney, Agent, or Firm*—Merton H. Douthitt; Gordon P. Becker

[57] ABSTRACT

Alkali metal oxides of cis- and trans-2,6,6-trimethylbicyclo(3.1.1)-heptan-2-ol are surprisingly effective bases in organic reactions calling for the use of a strong base, especially those reactions wherein abstraction of a proton from attachment to a carbon atom is postulated to occur in the mechanism.

3 Claims, No Drawings

ALKOXIDES OF 2-PINANOL

This application is a continuation-in-part of copending application Ser. No. 025,734, filed Mar. 30, 1979 and now abandoned.

BACKGROUND OF THE INVENTION

This invention relates to the use of alkoxides of 2-pinanol in organic chemical reactions calling for the use of a strongly basic agent. Typical of such agents is potassium tertiary butoxide, often in combination with a specially selected organic solvent such as dimethylsulfoxide. However, it has now been discovered that the alkali metal alkoxides of 2-pinanol are surprisingly stronger bases than the corresponding tertiary butoxides and other common alkoxides. Therefore, they ordinarily will be more effective for organic reactions calling for the use of strong base, particularly those reactions whose mechanisms are postulated to involve the abstraction of a proton from attachment to a carbon atom. Such reactions include elimination reactions (such as dehydrohalogenation), alkylation, condensation, carbene generation, carbanion formation, and transesterification. 2-Pinanol is bicyclic, and it tends to dehydrate under acidic conditions.

BROAD STATEMENT OF THE INVENTION

The invention is a process for performing an organic chemical reaction enhanced by the presence of strong base, which reaction is characterized by the use of an alkali metal-2,6,6-trimethyl-bicyclo(3.1.1)-heptan-2-oxide as said base. The alkali metal most desirable is sodium, potassium or lithium; it also can be cesium or rubidium.

DETAILED DESCRIPTION OF THE INVENTION

The instant alkoxides can be represented by the following general structure:

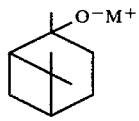

where $M^+$ represents alkali metal, the negative charge being on the pinanol depicted as an anion residue (i.e., a pinanol less its alcoholic hydrogen atom), the positive charge being borne by the alkali metal depicted as a cation. 2-Pinanol can be the cis or trans isomer of 2,6,6-trimethyl-bicyclo(3.1.1)-heptan-2-ol, or it can be a mixture of these isomers. For convenience herein, the alkoxides of pinanol often are referred to as "pinanoxides".

The potassium alkoxide of 2-pinanol previously has been suggested for reacting with methyliodide to prepare a methyl ether of pinanol. Alkali metal pinanoxides have also been mentioned as suitable to create basic conditions for the production of β-phellandrene (U.S. Pat. No. 4,136,126). Also, a magnesium alkoxide of pinanol has been made by a Grignard reaction. The pinanoxides for the instant invention can be prepared by reacting an elemental alkali metal or alkali metal hydride with 2-pinanol in a manner conventional for making alkali metal alkoxides of alkanols, and such preparation can be done prior to use or in situ in the chemical reaction mixture for which pinanoxide is being prepared. The pinanoxide also can be prepared by reacting an alkali metal hydroxide and 2-pinanol in an azeotropic solvent (i.e. one which can form a minimum-boiling azeotrope with water) at a temperature sufficient for removing the resulting solvent/water azeotrope formed from the reaction. East German Patent 100,701 provides further detail relative to this preferred method of preparing the pinanoxide. Suitable solvents which can form such azeotrope with the byproduct water of the reaction can be selected from the azeotrope table found in *The Handbook of Chemistry & Physics*, 47th Edition, pages D-1 to D-21, The Chemical Rubber Company, Cleveland, Ohio (1966), and incorporated herein by reference. Of course, use of only one solvent to form a binary azeotrope with water is not limiting to the process, as mixtures of solvents forming a ternary or more complex azeotrope with water can be used just as effectively for the instant purpose. Desirably, the azeotroping solvent will be stable to strong base and will be one which is effective to remove small quantities of water because water is a byproduct of the reaction to form the pinanoxide, and often only a small proportion of water is present in the reaction mixture, especially during the initial phase of this reaction. Suitable solvents include, by way of example and not of limitation, toluene, benzene, heptane, hexane, cymene and xylenes.

In summary, such preferred process for forming the pinanoxide is conducted by heating the reaction mixture of the 2-pinanol and alkali metal hydroxide in the azeotrope-forming solvent to a temperature sufficient to volatilize or distill the resulting water-bearing azeotrope from the mixture. The precise temperature or temperature range used in this process, of course, depends upon the particular solvent or solvents chosen for the reaction mixture and the resulting boiling point of the azeotrope which is formed with the byproduct water. While the 2-pinanol and alkali metal hydroxide all can be additionally charged to form the reaction mixture, it can be advantageous on occasion to add gradually or incrementally one or both of these components into the reaction mixture during the progress of this reaction. For present purposes, alkali metal includes sodium, potassium, rubidium, cesium, and lithium.

The pinanoxides proved valuable in a variety of chemical reactions which require use of a basic reagent. Such chemical reactions are enhanced by the presence of the basic agent either for increasing yields of the product, providing mild reaction conditions (for example, temperature and pressure), decreasing reaction time, and the like. It is entirely conceivable that the unusual base strength of the pinanoxides may permit practice of chemical reactions that heretofore were considered impractical because of poor yields, protracted reaction rates, otherwise unusually drastic reaction conditions or the like, and this is entirely consistent with and comprehended within the scope of the instant invention. Further, use of either the cis- or trans-pinanoxide can have decided benefit in certain chemical reactions as the examples will demonstrate.

An exceptional feature of the pinanoxides is that ordinarily no special solvent or mixture of solvents is required for use of the pinanoxide in chemical reactions. Potassium tertbutoxide, for example, often requires an aprotic, polar solvent, such as dimethylsulfoxide, in many chemical reactions. The instant pinanoxides frequently can be used alone or dispersed in the corresponding 2-pinanol from which they were prepared to good advantage in many chemical reactions, though use of such heretofore known special solvents can be desirable on occasion.

A unique feature of the instant pinanoxide bases is that they are the most basic alkoxides yet recorded. pKa measurements of the conjugate acids by the method of Bordwell [*J. Amer. Chem. Soc.*, 97, 7006 (1975)] gave the following data.

| Conjugated Acid | pKa in DMSO |
|---|---|
| t-Butanol | 30.4 |
| cis-Pinanol | 32.6 |
| trans-Pinanol | 32.8 |

A clearer understanding of the uniqueness of the instant use of these pinanoxides will be gained by reference to the following examples which detail how the present invention can be practiced but should not be construed as limiting the invention. In this application all temperatures are in degrees Centigrade, all percentages and proportions are on a molar basis, and all units are in the metric system, unless otherwise expressly indicated.

INTRODUCTION TO THE EXAMPLES

The reactions examined are typical reactions of organic chemicals requiring strong bases, e.g. elimination reactions, epoxide isomerization, olefin isomerization and alkylation reactions. Often reactions involving potassium, t-butoxide (t-BuOK) or other strong bases are run for comparison, or such data are presented from references.

It will be seen that generally the reactions illustrating the present invention are more complete or more rapid than similar reactions using other strong bases, and often the improvement is dramatic. Such dramatic improvements, it will be noticed, are often associated with the use of the alkali pinanoxide bases in a solvent composed of their respective alcohols. This preferred combination is not only surprisingly effective, but also allows an economical method of raising reaction temperatures (The pinanols reflux at about 195° C.) without the use of expensive high pressure apparatus.

INTRODUCTION TO EXAMPLES 1–8

Examples 1–5 relate to an elimination reaction wherein bornyl chloride 1 is dehydrochlorinated to make bornylene 2, as shown in Reaction 1:

Reaction 1

Bornyl Chloride → Bornylene
(Basic Agent)

The strength of the Basic Agent will largely determine the rate and degree of completion of this reaction.

Bornylene is a potential intermediate in the synthesis of camphor.

EXAMPLE 1

Under nitrogen, a dry 100 ml three-necked flask fitted with a condenser, addition funnel, thermometer, and magnetic stirrer was charged with 25 ml of freshly prepared 0.5 M potassium dimethylsulfoxide solution (Dimsyl$^-$K$^+$), and 12.9 mmoles of t-butanol was added to the solution with stirring. Then the flask was immersed in an oil bath at 70° C. until all of the Dimsyl$^-$K$^+$ had reacted forming potassium t-butoxide (t-BuOK) and leaving a slight excess of t-butanol. 2.13 g (12.5 mmoles) bornyl chloride was added. The reaction was sampled at intervals and analyzed by chromatography (GLC). The conversion was calculated from the ratio of bornyl chloride to α-fenchyl chloride. (Approximately 5% α-fenchyl chloride was present as an inert impurity in this and in most bornyl chloride.) The conversion was only 40.5% complete after 24 hours. Complete results are shown in Table 1.

EXAMPLE 2

In the procedure of Example 1, cis-pinanol was added in place of t-butanol, and it reacted to form potassium cis-pinanoxide (cis-PinanOK). In this case, the conversion proceeded to 59.7% completion in 24 hours, a substantial improvement. Complete results are shown in Table 1.

EXAMPLE 3

In the procedure of Example 1, trans-pinanol was added in place of t-butanol, and it reacted to form potassium trans-pinanoxide (trans-PinanOK). In this case, the conversion proceeded to 61.2% completion in 24 hours. Again, a substantial improvement. Complete results are shown in Table 1.

EXAMPLE 4

The procedure of Example 1 with the addition of NO alcohol to generate the alkoxide solution. Therefore, the only base present was Dimsyl$^-$K$^+$. Without the alkoxide present, the conversion was far less complete than with any of the alkoxide bases present. Results are shown in Table 1.

EXAMPLE 5

A 3-necked 100 ml flask was charged with 18 ml dimethylsulfoxide (DMSO) and 0.96 g (6.3 mmoles) 1,5-diazabicyclo [5.4.0] undec-5-ene(DBU), and then was heated with stirring to 70°. 1.08 g (6.3 mmoles) of bornyl chloride was added to the solution. Chromatography over a 24-hour period showed a maximum of 7.1% conversion, which is far less complete than for any of the alkoxides. Results are shown in Table 1.

TABLE 1

| DEHYDROCHLORINATION OF BORNYL CHLORIDE IN DMSO | | | | |
|---|---|---|---|---|
| Base | Temperature at Reflux | % Conversion after 1 Hour | % Conversion after 4 Hours | % Conversion after 24 Hours |
| t-BuOK | 70° C. | 14.8 | 24.0 | 40.5 |
| cis-PinanOK | 70° C. | 13.3 | 26.6 | 59.7 |
| trans-PinanOK | 70° C. | 15.9 | 32.4 | 61.2 |
| Dimsyl$^-$K$^+$ | 70° C. | 7.9 | 14.0 | 18.0 |
| DBU | 70° C. | 1.3 | 1.7 | 7.1 |

EXAMPLE 6

50 ml of a solution containing 40 mmoles of trans-PinanOK was prepared by reacting trans-pinanol with potassium hydride. At reflux (195° C.), 5 g (29.8 mmoles) of bornyl chloride dissolved in 5 g of n-decane was added. The reaction was monitored by gas chromatography using n-decane as an internal standard. Nearly complete conversion was obtained after one hour contrasted with a conversion of only 5% in 12 hours using t-BuOK reported by Borowiecki et al [*Bull. Chim. Soc., France*, 2364 (1967)]. Results are shown in Table 2.

EXAMPLE 7

The procedure of Example 6 wherein cis-pinanol and potassium metal were reacted to form a solution of cis-PinanOK. Again, nearly complete conversion was obtained after 1 hour. Results are shown in Table 2.

EXAMPLE 8

The procedure of Example 6 wherein trans-pinanol and sodium metal were reacted to form a solution of trans-PinanONa. Nearly complete conversion was obtained after 5 hours. Results are shown in Table 2.

EXAMPLE 9

2.3 mmoles of t-butanol was weighed into a 10 ml glass vial containing 1 ml of dry DMSO under nitrogen. 4 ml (0.53 M) of freshly prepared Dimsyl$^-$K$^+$ solution was added to the vial which was then sealed with a septum seal (Wheaton). The vial was placed in an oil bath at 70°. 0.15 g of diphenyl ether was added via syringe as the internal standard. After 20 minutes, 0.22 g (1.1 moles) of dichlorocamphane in 3.3 ml dry DMSO was added via syringe to the vial and the solution was shaken. The vial was also shaken when aliquots were removed for chromatographic analysis. After 24 hours, the conversion to bornadiene was 83% complete. Results are given in Table 3.

EXAMPLE 10

In the procedure of Example 9, cis-pinanol was used

TABLE 2

| | DEHYDROCHLORINATION OF BORNYL CHLORIDE IN ALCOHOLS | | | | | |
|---|---|---|---|---|---|---|
| Base | Temperature at Reflux | % Conversion after .17 Hours | % Conversion after .5 Hours | % Conversion after 1 Hour | % Conversion after 5 Hours | % Conversion after 12 Hours |
| cis-PinanOK | 197 | 60.5 | 87.3 | 94.8 | — | — |
| trans-PinanOK | 195 | 57.9 | 85.9 | 97.0 | — | — |
| trans-PinanOK | 195 | — | — | 44.0 | 92.4 | — |
| t-BuOK[1] | 83 | — | — | — | — | 5.0 |

[1] Reference data from Borowiecki et al, loc. cit.

INTRODUCTION TO EXAMPLES 9–16

Examples 9–16 relate to an elimination reaction wherein 2,6-dichlorocamphane 3 is di-dehydrochlorinated to make bornadiene 4 as shown in Reaction II.

Reaction II

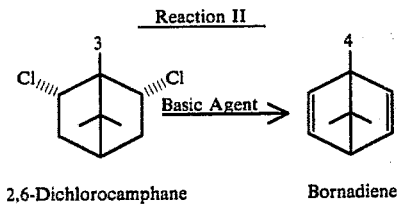

2,6-Dichlorocamphane     Bornadiene

This reaction was reported using t-BuOK in t-butanol by Kwart et al [*J. Amer. Chem. Soc.*, 78, page 5943 (1956)] and using Na-2-n-butylcyclohexoxide by Hanack et al [*Ann. Chem.*, 652, page 96 (1962)]. Na-2-n-butylcyclohexoxide and t-BuOK are both very strong bases, however, both references report that this reaction was difficult to achieve. In fact, Kwart et al reported no reaction after refluxing at 230° for 6 hours.

The marked contrast between these reports and the following examples will be clearly evident, especially when the solvent is the corresponding alcohol to the alkali pinanoxide base.

in place of t-butanol. After 24 hours, the conversion was 85.9% complete. Results are given in Table 3.

EXAMPLE 11

In the procedure of Example 9, trans-pinanol was used in place of t-butanol. After 24 hours, the conversion was 89.8% complete. Results are given in Table 3. For the second order reactions of Examples 9, 10, and 11, these results correspond to relative reaction rates of 1:3:9, respectively.

EXAMPLE 12

A 3-neck 100 ml flask was charged with 1.3 g (6.3 mmoles) dichlorocamphane and 30 ml dry toluene and 2 g dodecane as internal standard. The mixture was brought to reflux and 1.92 g (12.6 mmoles) DBU was added. The reflux temperature was 110° C. Refluxing continued for 24 hours during which samples were removed and analyzed by chromatography. After 24 hours, the conversion was only 7% complete. Results are given in Table 3.

EXAMPLE 13

In the procedure of Example 12, DMSO was used in place of toluene as solvent. In this case, the reaction temperature was 70° C., and the conversion obtained after 24 hours was 4%. Results are listed in Table 3.

TABLE 3

| | RESULTS OF EXAMPLES 9–13 | | | | |
|---|---|---|---|---|---|
| Base | Temperature of Reaction | % Conversion after 1 Hour | % Conversion After 4 Hours | % Conversion After 10 Hours | % Conversion After 24 Hours |
| t-Butoxide | 70 | 19.3 | 48.8 | 76.8 | 83.0 |
| cis-Pinanoxide | 70 | 22.1 | 51.3 | 79.0 | 85.9 |
| trans-Pinanoxide | 70 | 26.3 | 59.8 | 81.0 | 89.8 |
| DBU (in Toluene) | 110 | — | — | — | 7.0 |
| DBU (in DMSO) | 70 | — | — | — | 4.0 |

EXAMPLE 14

A 3-neck 100 ml flask was charged with 50 ml of cis-pinanol. 1.4 g (0.036 g atoms) of potassium metal was added and the flask was brought to reflux at 197° C. with stirring under nitrogen. When alkoxide formation was complete, 3.5 g (16.7 mmoles) dichlorocamphane was added to the reaction. Using gas chromatography, conversions were calculated with cis-pinanol as the internal standard. The use of cis-PinanOK gave nearly complete conversion of dichlorocamphane to bornadiene in 12 minutes. This is in sharp contrast to no conversion or very difficult conversions reported in previous references. Results are given in Table 4.

EXAMPLE 15

In the procedure of Example 14, trans-pinanol was used in place of cis-pinanol. Again, nearly complete conversion was obtained in 12 minutes. Results are given in Table 4.

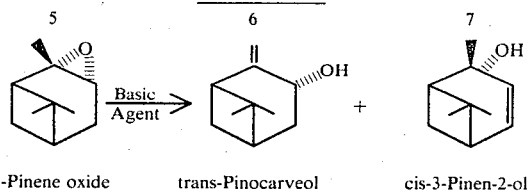

Reaction IV

α-Pinene oxide → trans-Pinocarveol + cis-3-Pinen-2-ol

The pseudo-first order rate constants for these reactions in DMSO were calculated and will show faster isomerization by the pinanoxide bases than t-BuOK.

EXAMPLE 17

6.3 ml (1.1 M) of a Dimsyl$^-$K$^+$ solution was added to a 10 ml vial containing 0.71 mmoles of t-butanol. After equilibration at 70°, 0.21 g (0.14 mmoles) of α-pinene oxide was added via a syringe. The vial was shaken thoroughly and shaken again when samples were removed for chromatographic analysis. The rate constant for this reaction was calculated, and this rate constant and the results are shown in Table 6.

TABLE 4

RESULTS OF EXAMPLES 14 AND 15

| Base | Temperature of Reflux | % Conversion after 3 Min. | % Conversion after 7 Min. | % Conversion after 12 Min. | % Conversion after 6 Hours |
|---|---|---|---|---|---|
| trans-PinanOK | 195 | 92.6 | 98.0 | 99.0 | — |
| cis-PinanOK | 197 | 81.5 | 89.0 | 96.0 | — |
| t-BuOK[1] | 230 | — | — | — | 0 |

[1]Kwart et al, loc. cit.

EXAMPLE 16

In the procedure of Example 15, sodium metal was used in place of potassium metal to form trans-PinanONa. Here, the conversion took 55 minutes to go to 98.9% of completion, again, a sharp contrast to previously reported data.

EXAMPLE 18

In the procedure of Example 17, cis-pinanol was used in place of t-butanol. Again, the rate constant for this reaction is calculated, and this rate constant and the results are shown in Table 6.

TABLE 5

RESULTS OF EXAMPLE 16

| Base | Temperature of Reflux | % Conversion after 15 Min. | % Conversion after 26 Min. | % Conversion after 55 Min. | % Conversion after 6 Hours |
|---|---|---|---|---|---|
| trans-PinanONa | 195 | 80.3 | 90.5 | 98.9 | — |
| t-BuOK[1] | 230 | — | — | — | 0 |

[1]Kwart et al, loc. cit.

INTRODUCTION TO EXAMPLES 17–23

The isomerization of α-pinene oxide 5 has been described in the literature by Z. Rykowski et al, [*Roczniki, Chem.*, 48, 1619 (1974)] and J. P. Montheard et al, [*Bull. Soc. Chim. France*, 336 (1968)]. They reported this reaction as yielding pinocarveol 6 exclusively when reacted with t-BuOK in DMSO or DMF.

In Examples 17–19, this reaction was repeated with t-BuOK, cis-PinanOK and trans-PinanOK in DMSO at 70°. Two products were observed (trans-pinocarveol 6 and cis-3-pinen-2-ol 7) in all cases (see Reaction IV). Similar distributions of these products will be seen in Examples 21–23 indicating that potassium pinanoxides react in the same manner as t-BuOK.

EXAMPLE 19

In the procedure of Example 17, trans-pinanol was used in place of t-butanol. Again, the rate constant for this reaction was calculated and is shown with the results in Table 6.

EXAMPLE 20

The reaction of Example 17 was also carried out with t-BuOK in DMSO at 90° following the procedure described by Montheard et al, loc. cit. In this case, the α-pinene oxide concentration was 0.77 M. and the t-BuOK concentration was 0.85 M. The same products were obtained from this reaction as for the reaction in Example 17, contrary to the reported results which showed only the formation of pinocarveol. Results are shown in Table 6.

TABLE 6
ISOMERIZATION OF α-PINENE OXIDE

| Base | Temp. °C. | Time Hrs. | % α-Pinene Oxide | % Pino-car-veol | % cis-30 Pi-nen-2-ol | Rate Constant k sec$^{-1}$ × 10$^4$ |
|---|---|---|---|---|---|---|
| t-BuOK[a] | 70 | 1 | 40.1 | 44.0 | 15.9 | — |
|  |  | 2 | 14.7 | 63.4 | 21.9 | 2.75 |
| cis-PinanOK[a] | 70 | 1 | 37.4 | 45.6 | 17.0 | — |
|  |  | 2 | 14.0 | 63.2 | 22.8 | 2.78 |
| trans-PinanOK[a] | 70 | 1 | 24.6 | 49.2 | 26.2 | — |
|  |  | 2 | 6.4 | 62.5 | 31.1 | 3.67 |
| t-BuOK[b] | 90 | 48 | — | 62.1 | 37.9 | — |

[a] [epoxide] = 0.22 M, [Base] = 1.1 M
[b] [Epoxide] = 0.77 M. [base] = 0.85 M, by procedure of Montheard et al

EXAMPLE 21

5.18 g (28.5 mmoles) of a 22% potassium hydride solution in mineral oil was washed three times with 5 ml of pentane under nitrogen to remove the mineral oil. 4.4 g (28.8 mmoles) of cis-pinanol was carefully added to the suspension and after the addition was complete, the excess pentane was removed under vacuum. 28 ml of dry DMF was then added. When the reaction reached 115°, 1 g (6.5 mmoles) of α-pinene oxide was added. The results show complete reaction in 1 hour, and the product contained 72.1% pinocarveol and 27.9% cis-3-pinen-2-ol.

EXAMPLE 22

In the procedure of Example 21, trans-pinanol was used in place of cis-pinanol. The results again show complete reaction in one hour, and the product contained 67.7% pinocarveol and 32.3% cis-3-pinen-2-ol.

EXAMPLE 23

1.0 g (6.5 mmoles) of α-pinene oxide was added to a 115° solution containing 3.2 g (28.5 mmoles) of t-butoxide and 28 ml of DMF. After 1 hour, chromatographic analysis showed the starting material had reacted and the product contained 71.4% pinocarveol and 28.8% cis-3-pinen-2-ol. Note the similar product ratios obtained in Examples 21–23.

INTRODUCTION TO EXAMPLES 24–27

The isomerization of limonene 8 with t-butoxide has been described by Bank et al, [J. Org. Chem., 33, 221 (1968)] the disclosure of which is expressly incorporated herein by reference. This reaction was re-examined with t-BuOK, cis-PinanOK, and trans-PinanOK salts in DMSO at 60°. In essence, this reaction is represented by Reaction V. It will be seen in these examples that the pinanoxide bases give significantly faster reaction than t-BuOK.

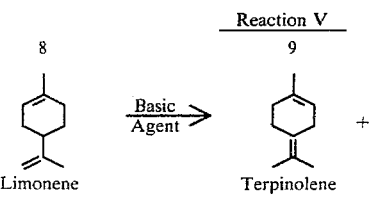

Reaction V
8 → 9
Limonene → Terpinolene (Basic Agent) +

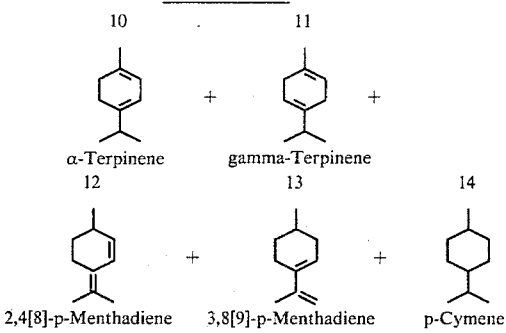

-continued
Reaction V

10 + 11 + α-Terpinene 12 + gamma-Terpinene 13 + 14

2,4[8]-p-Menthadiene + 3,8[9]-p-Menthadiene + p-Cymene

EXAMPLE 24

The isomerization in DMSO at 60° was carried out by the method of Bank et al. The concentrations of t-BuOK and limonene used were 0.6 M and 0.4 M, respectively. The reaction was allowed to proceed for 48 hours. The identities of the reaction products were obtained by gas liquid chromatography retention time and gas chromatography-mass spectroscopy comparison with authentic samples. The results are given in Table 7.

EXAMPLE 25

In the procedure of Example 24, cis-PinanOK was substituted for t-BuOK. These results are also shown in Table 7.

EXAMPLE 26

In the procedure of Example 24, trans-PinanOK was substituted for t-BuOK. These results are also given in Table 7.

TABLE 7
ISOMERIZATION OF LIMONENE

| Base | % 8 | % 9 | % 10 | % 11 | % 12 | % 13 | % 14 | k Sec$^{-1}$ × 10$^6$ | k Rel |
|---|---|---|---|---|---|---|---|---|---|
| trans-PinanOK | 9.1 | 1.0 | 42.6 | 13.6 | 27.9 | 3.0 | 2.8 | 14.0 | 3.3 |
| cis-PinanOK | 37.6 | 0.9 | 29.0 | 9.6 | 19.1 | 2.5 | 1.3 | 5.6 | 1.3 |
| t-BuOK | 46.6 | 0.5 | 24.7 | 8.3 | 16.1 | 2.1 | 1.7 | 4.2 | 1.0 |

EXAMPLE 27

Into a stirred, 3-neck glass vessel fitted with a trap and condenser, were added 50 g of limonene, 26 g of KOH and 100 g of a pinanol mixture containing approximately 75% cis- and 25% trans-pinanols. The reaction was brought to reflux at 190° C. The liberated water was collected in the trap. After 48 hours of reflux, a sample of oil distillate was removed from the upper layer of the trap. By gas chromatographic analysis, it was found to contain 17.7% α-pinene, 4.5% α-terpinene, 4.0% limonene, 37.2% cymene, 8.5% minor unidentified compounds.

INTRODUCTION TO EXAMPLES 28–30

Example 28 relates to the isomerization of vinylnorbornene 15 to ethylidenenorbornene 16.

Reaction VI

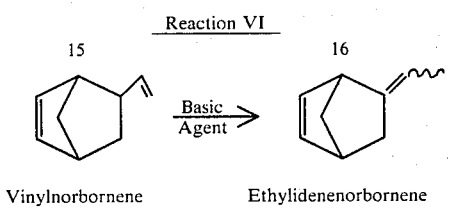

Vinylnorbornene → Ethylidenenorbornene

This isomerization of an olefin is described by Fritz et al in U.S. Pat. No. 3,347,944 and shown to require a dipolar aprotic solvent (e.g. DMSO) in combination with t-BuOK in order to effect the isomerization. It will be seen that the isomerization of vinylnorbornene in DMSO can be carried out using a base according to the present invention. Also, it should be observed that the isomerization will proceed to a greater extent using such base.

EXAMPLE 28

In the procedure of Example 24, vinylnorbornene was used in place of limonene, and the reaction temperature was lowered to 50°. The results are given in Table 8.

EXAMPLE 29

In the procedure of Example 28, cis-PinanOK was used in place of t-BuOK. Again, the reaction temperature was lowered to 50°. The results are shown in Table 8.

EXAMPLE 30

In the procedure of Example 29, trans-PinanOK was used in place of cis-PinanOK. These results are also given in Table 8.

TABLE 8

ISOMERIZATION OF VINYLNORBORNENE IN DMSO AT 50°

| Base | Time Hrs. | % Vinylnorbornene | % Ethylidenenor- bornene |
|---|---|---|---|
| t-BuOK | 23 | 18.2 | 81.8 |
| cis-PinanOK | 23 | 16.4 | 83.6 |
| trans-PinanOK | 23 | 8.7 | 91.3 |

INTRODUCTION TO EXAMPLE 31

This example relates to the isomerization of α-pinene to β-pinene.

Reaction VII

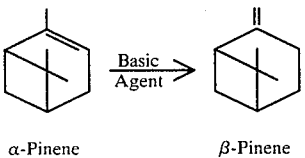

α-Pinene → β-Pinene

In U.S. Pat. No. 3,278,623, column 8, lines 31–34, an example of this isomerization was described as follows:
"The catalyst was sodium metal and the charge pure α-pinene. Operation at 200° C. for 4 hours. The isomerizate analyzed 4.5% β-pinene, 3% limonene and the balance α-pinene."

In Example 31, it will be demonstrated that for this reaction, trans-PinanOK is at least as strong a base as sodium metal.

EXAMPLE 31

Into a stirred, 3-neck, glass reaction vessel, fitted with a trap and condenser, were added 18 g of trans-pinanol, 4.4 g of KOH and 5.0 g of α-pinene. The reaction was brought to reflux at 180° C.; the small amounts of water liberated were allowed to collect in the trap. Samples were removed at intervals, washed with sodium bicarbonate solution, analyzed by gas chromatography, and gave the following results.

TABLE 9

| Time (Hrs.) | α-Pinene | βPinene | p-Menthadienes |
|---|---|---|---|
| 1.00 | 96.92 | 2.23 | 0.86 |
| 3.00 | 94.57 | 4.57 | 0.90 |
| 4.75 | 94.04 | 4.79 | 1.17 |

INTRODUCTION TO EXAMPLE 32

Example 32 relates to the isomerization of 3-carene to 2-carene.

Reaction VIII

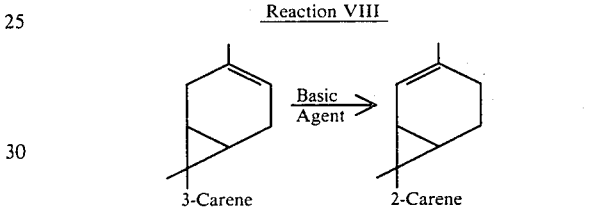

3-Carene → 2-Carene

This isomerization is known to take place only in the presence of a very strong base, and even then, will only proceed to a limited extent.

EXAMPLE 32

Into a stirred, 3-neck glass reaction vessel fitted with a trap and condenser were added 50 g of 3-carene (92% 3-carene, 1% 2-carene), 100 g of cis-pinanol, and 25 g of KOH. The reaction was brought to reflux at 185° C.; the water formed as a result of alkoxide formation was allowed to collect in the trap. Samples were removed at intervals, washed with sodium bicarbonate solution, analyzed by gas chromatography and gave the following results:

TABLE 10

| Hours | % 2-Carene in Total Carenes |
|---|---|
| 0 | 1.0 |
| 2 | 1.4 |
| 5 | 3.2 |
| 13 | 4.0 |
| 32 | 9.9 |

INTRODUCTION TO EXAMPLES 33-35

These examples relate to the ketone alkylations comprising the addition of n-butyl iodide to ethyl acetoacetate. Such reaction is reported in a study done by Renfrow et al [J. Amer. Chem. Soc., 68, page 1801 (1946)] to require a very strong base to proceed. It will be seen in these examples that the potassium pinanoxide bases of the present invention will react equivalently with the potassium butoxide base reported by Renfrow et al. In interpreting these results, it should be kept in mind that the yields obtained are virtually quantitative and any variation can easily be attributable to analytical error.

EXAMPLE 33

25 g of a suspension of 22% potassium hydride in mineral oil was washed twice with pentane and then with dry tetrahydrofuran (THF) under nitrogen, in order to remove the mineral oil. To the washed hydride was added 15.6 g (0.082 moles) of trans-pinanol in 100 ml of dry THF. After the evolution of hydrogen had ceased, 10.6 g (0.82 moles) of ethyl acetoacetate and 10 g of n-decane (as internal standard) in 100 ml of THF were added to the stirred alkoxide solution. After the exothermic reaction had subsided, the reaction was heated to reflux and n-butyl iodide was added to the refluxing reaction mixture. The reaction mixture was stirred vigorously at reflux, and aliquots were removed at intervals and titrated with a standardized acid solution to determine the rate of reaction. This reaction was at least 90% complete within two hours and showed second order kinetics with accompanying precipitation of metal iodide. The yield of ethyl n-butyl acetoacetate was determined to be 93.8%.

EXAMPLE 34

In the procedure of Example 33, cis-pinanol was used instead of trans-pinanol. The yield of ethyl n-butyl acetoacetate was determined to be 93.5%.

EXAMPLE 35

In the procedure of Example 33, t-BuOK was used instead of potassium hydride and trans-pinanol. In this case, the yield of ethyl n-butyl acetoacetate was determined to be 96.6%.

SUMMARY OF THE EXAMPLES

In summary, alkali pinanoxides have been shown to be extraordinarily strong bases and useful in reactions requiring hydrogen abstraction from attachment to a carbon atom. All of the examples show such reactions. Often alkali pinanoxides react faster and to a greater extent than other known strong bases. However, their reactions occur in a similar manner. Having amply demonstrated this extraordinary strength as bases in a variety of organic reactions requiring hydrogen abstraction by a strong basic agent, we do not intend that these examples be construed as limiting, but that the invention be given broad scope as defined in the following claims.

What is claimed is:

1. A method of improving the reaction rate or yield of an organic chemical reaction which can be affected only under basic conditions wherein said reaction is an elimination reaction which comprises, contacting the reactants of said organic chemical reaction with a pinanoxide base, said base being an alkali metal-2,6,6-trimethyl-bicyclo(3.1.1)-heptan-2-oxide.

2. The process of claim 1 wherein said base is borne in a vehicle of 2,6,6-trimethyl-bicyclo(3.1.1)-heptan-2-ol.

3. The process of claim 2 wherein said base and said alcoholic vehicle are of the same isomeric configuration.

* * * * *

UNITED STATES PATENT AND TRADEMARK OFFICE
CERTIFICATE OF CORRECTION

PATENT NO. : 4,289,917
DATED : Sept. 15, 1981
INVENTOR(S) : Bernard J. Kane and Sean G. Traynor It is certified that error appears in the above-identified patent and that said Letters Patent are hereby corrected as shown below:

Column 5, Table 2, line 26, "trans-PinanOK" should read
--trans-PinanONa--.

Column 9, Table 6, line 4, the subheading "% cis-30 Pinen-2-ol"
should read --% cis-3-Pinen-2-ol--.

Column 10, Reaction V, the last formula (14)

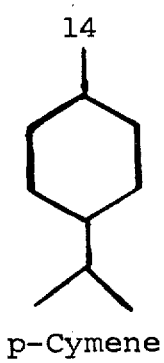

p-Cymene should read

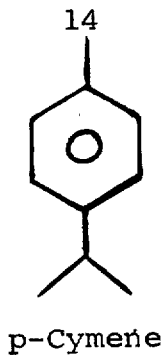

p-Cymene

Signed and Sealed this

First Day of December 1981

[SEAL]

Attest:

GERALD J. MOSSINGHOFF

Attesting Officer    Commissioner of Patents and Trademarks